atent Number: 5,455,049

United States Patent [19]
Anaebonam et al.

[45] Date of Patent: Oct. 3, 1995

[54] TERFENADINE ORAL POWDER

[75] Inventors: Aloysius O. Anaebonam, Burlington, Mass.; Abdel A. Fawzy, Nashua, N.H.; Emmett Clemente, Manchester, Mass.

[73] Assignee: Ascent Pharmaceuticals, Inc., Billerica, Mass.

[21] Appl. No.: 368,421

[22] Filed: Jan. 4, 1995

[51] Int. Cl.⁶ ............................................. A61K 9/16
[52] U.S. Cl. ................... 424/499; 424/439; 424/489; 424/497; 424/501
[58] Field of Search ............................ 424/499, 439, 424/489, 497, 501

[56] References Cited

U.S. PATENT DOCUMENTS

| | | | |
|---|---|---|---|
| 4,957,932 | 9/1990 | Young et al. | 514/375 |
| 5,250,529 | 10/1993 | Theoharides | 514/255 |
| 5,375,693 | 12/1994 | Woosley et al. | 514/317 |

*Primary Examiner*—Thurman K. Page
*Assistant Examiner*—S. Howard
*Attorney, Agent, or Firm*—Welsh & Katz, Ltd.

[57] ABSTRACT

The present invention contemplates a dry, powdered terfenadine composition. That composition comprises (a) a mixture of:
  (i) about 1 to about 20 parts by weight micronized terfenadine and
  (ii) about 0.2 to about 10 parts by weight a polyethylene oxide-polypropylene oxide-polyethylene oxide block copolymer having an HLB number of 24 that is a wetting agent for said terfenadine;

that are dry-blendedly dispersed into:

(b) about 20 to about 40 parts by weight spray-dried sorbitol particles that are loosely packed, randomly oriented filamentary crystals having pores that entrap said terfenadine particles and wetting agent upon said dry-blended dispersal, said components being further dry blended with (c) about 2 to about 10 parts by weight dry polyvinylpyrrolidone;

(d) about 1 to about 5 parts by weight of a dry mixture of microcrystalline cellulose and sodium carboxymethylcellulose; and (e) a dry flavorant in an amount sufficient to provide a desired taste to said powder;

said composition being a free-flowing powder that is substantially free from the taste of terfenadine when placed on the human tongue in dry form or when dispersed in water and tasted within about five minutes of said dispersal.

8 Claims, No Drawings

TERFENADINE ORAL POWDER

DESCRIPTION

1. Technical Field

The present invention relates to an orally administrable antihistamine-containing powder, and more particularly to an orally administrable, pleasant tasting powdered form of terfenadine that when applied to the tongue is substantially free of the taste of solubilized terfenadine.

2. Background Art

Terfenadine is a well-known antihistamine that is a selective antagonist of the histamine $H_1$-receptor. Terfenadine lacks sedative properties. This particularly effective drug has a particularly offensive taste when dissolved and is consequently formatted for oral administration as a pill or tablet that minimizes that offensive taste.

Although provision in a tablet form overcomes the problem of offensive taste for this valuable medicament for most of the adult population that uses terfenadine, many adults and many children have difficulty swallowing the pills or tablets or cannot swallow them, and thereby do not benefit from terfenadine.

The disclosure that follows illustrates one solution to the problem of terfenadine delivery that is applicable to adults and children that cannot swallow capsules or have difficulty doing so, as well as an alternative delivery mode for the general population.

BRIEF SUMMARY OF THE INVENTION

A dry, powdered terfenadine composition is contemplated. That composition comprises (a) a mixture of:
   (i) about 1 to about 20 parts by weight micronized terfenadine, and
   (ii) about 0.2 to about 10 parts by weight a polyethylene oxide-polypropylene oxide-polyethylene oxide block copolymer having an HLB number of about 24 that is a wetting agent for the terfenadine;

Those components are jointly dry-blendedly dispersed into:

(b) about 20 to about 40 parts by weight spray-dried sorbitol particles. The particles are loosely packed, randomly oriented filamentary crystals having pores that entrap the micronized terfenadine particles and wetting agent upon dry-blended dispersal. The three blended components are further dry blended with (c) about 2 to about 10 parts by weight dry polyvinylpyrrolidone;

(d) about 1 to about 5 parts by weight dry microcrystalline cellulose that includes sodium carboxymethylcellulose; and (e) a dry flavorant in an amount sufficient to provide a desired taste to the powdered composition;

The resulting composition is a free-flowing powder that is substantially free from the taste of solubilized terfenadine when placed on the human tongue in dry form or when dispersed in water and tasted within about five minutes of the dispersal.

The present invention has several benefits and advantages.

One benefit is that the terfenadine oral powder disclosed can be taken by those persons that have difficulty swallowing usually supplied pills or tablets, or cannot so swallow without experiencing the offensive taste usually associated with solubilized terfenadine.

An advantage of the invention is that the terfenadine oral powder can also be dispersed in foods or aqueous liquids and consumed without exhibiting the usual offensive taste of solubilized terfenadine.

Another benefit of the invention is that the powdered composition, once placed onto the tongue, disperses almost immediately, without having a gritty or other noticeable residue.

Another advantage of the invention is that use of dry granulation procedures provides enhanced efficiency in manpower and energy usage compared to a liquid mixing procedure in that no drying step is required.

Still further benefits and advantages of the present invention will be apparent to the worker of ordinary skill from the disclosure that follows.

DETAILS DESCRIPTION OF THE INVENTION

The present invention contemplates a free-flowing powdered form of terfenadine that is pleasant tasting, substantially free from the usual taste of solubilized terfenadine, and is designed to be taken orally as by administration of the powder directly into the mouth or upon reconstitution in a small amount of water or in food.

A contemplated composition comprises (a) a mixture of (1) about 1 to about 20 parts by weight of micronized terfenadine and (ii) about 0.2 to about 10 parts by weight of a polyethylene oxide-polypropylene oxide-polyethylene oxide block co-polymer having an HLB number of about 24 that is a wetting agent (dispersant) for the terfenadine;

(b) about 20 to about 40 parts by weight spray-dried sorbitol particles, a loosely packed, randomly oriented filamentary crystals having pores that entrap the micronized terfenadine particles and wetting agent upon the dry-blended dispersal. The dry blended (a) and (b) components are further dry blended with (c) about 2 to about 10 parts by weight dry polyvinylpyrrolidone;

(d) about 1 to about 5 parts by weight dry microcrystalline cellulose; and (e) a dry flavorant in an amount sufficient to provide a desired pleasant taste to the powdered composition.

The resulting powdered composition is free-flowing and is substantially free from the taste of solubilized terfenadine when placed on the human tongue in dry form or when dispersed in water and tasted within about five minutes of that dispersal.

A contemplated composition contains both micronized terfenadine and a spray-dried sorbitol. Those materials can be present at a weight ratio of 1:20 to about 1:2 terfenadine-:sorbitol. That weight ratio is more preferably about 1:12.5 to about 1:3.5, and most preferably is about 1:10 in the order noted.

The wetting agent block co-polymer assists in dispersing the micronized terfenadine, but does not form micellular structures that solubilize the terfenadine. The wetting agent is present at about one-fifth to about one-half the weight of the micronized terfenadine, and more preferably at about one-half the weight of terfenadine.

Polyvinylpyrrolidone (PVP; povidone) that acts as a debittering agent to the terfenadine and secondarily can assist in building viscosity and mouth feel is present at a weight ratio to the sorbitol particles of about 1:10 to about 1:4 of PVP:sorbitol.

A mixture of microcrystalline cellulose and sodium carboxymethylcellulose that acts as a wetting agent for the blended materials is also present. This cellulosic mixture is present at a weight ratio of about 20 to about 1:8 relative to the sorbitol. More preferably, that weight ratio is about 1:12 to about 1:9; with a weight ratio of about 1:10 being most preferred.

The composition also contains a flavorant that can be a single ingredient such as fructose or sucrose or both, or more complex mixtures of materials that provide a desired pleasant sweetness or other flavor than that of solubilized terfenadine itself. The composition is substantially free from a solubilized terfenadine taste and has a pleasant, non-medicinal taste.

The composition is also free-flowing in that its individual particles tend not to clump together or agglomerate even when in the mouth or stirred in an amount of water sufficient to form a watery suspension, as compared to a paste or cream. The dry composition therefore flows freely when poured from one vessel to another.

Turning more specifically to the individual ingredients, the terfenadine used herein is terfenadine USP that has been finely comminuted into micron-sized particles. The terfenadine is therefore often referred to herein as "micronized" to highlight its small particle size, and at other times hereinafter that material is called terfenadine. This micronized terfenadine is sized so that 100 percent of the particles are less than 10 µm, and at least 85 percent are smaller than 5 µm. Typical bulk densities for this material are about 0.1 to about 0.5 g/ml.

Micronized terfenadine is available from several commercial sources. Illustrative sources include CiLag AG Schalfhausen, Switzerland (Zetapharm, Inc. of New York, N.Y.); and Erregirre Industrial Chimiea, SpA, Italy (Flavine International Inc. of Closter, N.J.).

The usual antihistaminic dosage of terfenadine for adults and children over 13 years of age is 60 mg twice each day. For younger children, the dosage is usually about 15–30 mg twice each day.

As used here, a single dose of powdered composition having a total mass of 0.5, 1 or 2 grams is designed to carry the entire antihistaminic amount of terfenadine. As a consequence, the amounts of ingredients other than micronized terfenadine are based upon the amount of terfenadine preferably being calculated to be a dose of about 15, 30 or 60 mg. It should also be understood that less than the usual antihistaminic amount can be used in a single dose with several doses being supplied at about the same time or within about one hour of each other to provide an antihistaminic amount of terfenadine.

Thus, a powdered composition, when viewed only as a composition, need only define relative amounts by parts or other ratios of each ingredient to another ingredient or ingredients. However, when used to supply an antihistaminic amount of terfenadine, or contemplated in a process for use or treatment, total amounts of ingredients are considered.

In a given composition, micronized terfenadine is present at about 1–20 parts. More preferably, the micronized terfenadine is present at about 2–10 parts, and most preferably at about 3 parts by weight.

A contemplated polyethylene oxidepolypropylene oxide-polyethylene oxide block copolymer wetting agent is referred to in the nomenclature of the *International Cosmetic Ingredient Dictionary*, 5th ed., Menninger et al., eds., The Cosmetic, Toiletry, and Fragrance Association, Washington, D.C. (1993) as a "Poloxamer", followed by a numerical designation. A particular Poloxamer of interest here contains polyethylene oxide blocks of about equal average length on either side of the polypropylene oxide block, with the average total molar ratio of oxyethylene to oxypropylene repeating groups in each molecule being about 5 to about 6. These materials are all solids at ambient room temperature and have an HLB of 24.

Exemplary Poloxamer wetting agent molecules are sold under the trademark PLURONIC polyol F-38, F-68, F-88, F-98 and F-108 for Poloxamers 108, 188, 238, 288 and 338, respectively. Pluronic polyol F-68 is particularly preferred. These Pluronic polyols are available from BASF Corporation of Mount Olive, N.J.

The Poloxamer is present at about one-fifth to about one-half the weight of the micronized terfenadine, with more of the Poloxamer wetting agent being used when more micronized terfenadine is used. Thus, where the powder composition contains about 1 to about 20 parts micronized terfenadine, about 0.2 to about 10 parts Poloxmer wetting agent are also present. With a more preferred amount of terfenadine of about 2 to about 10 parts, one uses about 1 to about 5 parts Poloxmer, and most preferably, about 1.5 parts Poloxmer are used with 3 parts micronized terfenadine.

The spray-dried sorbitol is a specialized product produced by E. Merck of Darmstadt, and available from EM Industries Inc. of Hawthorne, N.Y. under the trademark sorbitol Instant™. Sorbitol Instant™ is spray-dried from an aqueous solution and whereas crystalline sorbitol exhibits sharp angles, a smooth particle surface and provides a gritty texture and mouth feel when tableted, sorbitol Instant™ is comprised of loosely packed, randomly oriented, interwoven filamentary crystal particles. Magnification of those particles shows pore spaces within the particles and a furry-looking particle surface appearance. Any reference to "sorbitol" herein except a specific reference to the usual "crystalline sorbitol" is to sorbitol Instant™.

Sorbitol is known to have a high capacity to adsorb some small drug particles, with the adsorption being dependent upon particle size as well as electrostatic and Van der Waals forces. Thus, some drugs such as acetaminophen do not form adsorbates to a high degree, whereas others such as erythromycin ethylsuccinate form very concentrated adsorbates.

Two forms of sorbitol Instant™ are commercially available, and both can be used herein. The first is referred to as 7703 sorbitol Instant™ Pharma, which is preferred, and the second is referred to as 11578 sorbitol Instant™ P3000. Both products are soluble at 360 g/100 ml water at 40° C. and have a specific rotation, $[\alpha]_D^{20}$ (C.=1, water, borato complex) of +4.0° to +7.0°, calculated as the anhydrous material that it is.

The two materials differ in particle size and therefore bulk density. 7703 Sorbitol Instant™ Pharma has the following particle size distribution: <212 µm (70 mesh) <5 percent, <500 µm (35 mesh) <80 percent; and 850 µm (20 mesh) <5 percent, with a bulk density of 38–46 g/100 ml and a tapped density of 45–50 g/100 ml. 11578 Sorbitol Instant™ P3000 has the following particle size distribution: <53 µm (270 mesh) <15 percent, 53–106 µm (270–140 mesh) 15–20 percent, 106–212 µm (140–70 mesh) 40–50 percent, 212–500 µm (70–35 mesh) 20–30 percent, and >500 µm (35 mesh) <1 percent, with a bulk density of 45–55 g/100 ml and a tapped density of 51–56 g/100 ml. Sieve sizes are U.S. Standard Sieve Series.

The sorbitol is used in excess over the terfenadine so that when more terfenadine is present, more sorbitol Instant™ is used. A preferred composition that contains 1 to about 20 parts micronized terfenadine therefore contains about 20 to about 40 parts sorbitol. A preferred composition containing about 2 to about 10 parts terfenadine contains about 25 to about 35 parts sorbitol Instant™, whereas a most preferred composition that contains about 3 parts terfenadine contains about 30 parts sorbitol.

Sorbitol can also be used in greater amounts to provide bulk to the composition. Any excess in the amount of sorbitol over the weight ratio to terfenadine discussed hereinbefore is so used, as compared to the primary use of sorbitol Instant™ as a dispersing and taste-masking agent for the terfenadine.

The micronized terfenadine and block copolymer wetting agent are dry-blendedly dispersed into the sorbitol. That is, the first two ingredients are blended dry with each other and with the sorbitol Instant™, and adhere to the sorbitol and fill its pores. This is preferably accomplished by a tumbling mixer with the fortunate result that both the terfenadine and block copolymer adhere to the sorbitol particles without greatly changing the particle size of the sorbitol except for the size increase due to the adsorption and without noticeable agglomeration of filled and coated sorbitol particles. This lack of agglomeration contributes to the free flowing character of the final powder composition.

The above dry blended components are thereafter dry blended further with dry PVP, dry microcrystalline cellulose and a dry flavorant, as are discussed below.

The polyvinylpyrrolidone (PVP) is a well known item of commerce that is available in several molecular weight grades from several suppliers. A particularly preferred material is sold under the trademark KOLLIDON by BASF Corp. of Mount Olive, N.J. Exemplary materials are sold as KOLLIDON 25, 30 and 90 that have weight average molecular weights of about 25,700, 42,500 and 1,100,000, respectively. These materials are free flowing powders with particle sizes in the range of about 50 to about 250 μm. Particles smaller than 50m are present at less than 10 percent for all grades, and particles greater than 250 μm are less than 5 percent for KOLLIDON 25 and 30, and less than 20 percent for KOLLIDON 90. Bulk densities are about 0.40–0.50 g/ml, 0.35–0.50 g/ml and 0.40–0.50 g/ml for KOLLIDON 25, 30 and 90, respectively.

The highest molecular weight material, KOLLIDON 90, is preferred herein. This material, unexpectedly and primarily, provides a further taste-enhancing, de-bittering function to the terfenadine. Secondarily, the PVP also provides an enhanced mouthfeel when the composition is on the tongue, and additionally provides body (viscosity) when the composition is reconstituted in water.

The PVP is used at a weight ratio of about 1:10 to about 1:4 to sorbitol. More of the PVP is used when more terfenadine and sorbitol are in the composition. Thus, about 20 to about 40 parts sorbitol are used with about 2 to about 10 parts of PVP. More preferably, about 25 to about 35 parts sorbitol are used with about 3 to about 7 parts PVP. Most preferably, about 30 parts of sorbitol are used with about 5 parts of PVP.

A mixture of microcrystalline cellulose and sodium carboxymethylcellulose (NaCMC) is also utilized in the composition as a colloidal suspending agent. The NaCMC is present at about 7 to about 20 weight percent in this mixture so the mixture is more simply referred to as microcrystalline cellulose as that material constitutes about 80 to about 93 percent of the total. This material is listed in the *U.S. Pharmacopeia National Formulary* as microcrystalline cellulose and carboxymethylcellulose sodium.

A preferred mixture is available from FMC Corporation, Philadelphia, Pa. under the trademarks AVICEL RC-501, RC-581, RC-591 and CL-611. These materials are solid powders that pass through a 60 mesh sieve to at least 99.9 percent and are retained on a 200 mesh sieve at not more than 40 and 35 weight percents (AVICEL RC-501 and RC-581, respectively), or 45 and 50 percents on a 325 mesh sieve (AVICEL RC-591 and CL-611, respectively). The two first designated materials typically require high shear mixing for dispersion in water, whereas the latter two materials only require moderate shear for dispersion.

AVICEL CL-611 is preferred herein and forms a thixotropic gel in water when present at greater than 1.2 percent. This material contains about 11 to about 19 percent NaCMC.

The microcrystalline cellulose mixture is present at a weight ratio of about 1:20 to about 1:8 relative to the sorbitol. As more terfenadine and sorbitol are used, more of the microcrystalline cellulose is also used. Thus, where about 20 to about 40 parts sorbitol are present, about 1 to about 5 parts of microcrystalline cellulose are also present. More preferably, about 25 to about 35 parts sorbitol are used with about 2 to about 4 parts microcrystalline cellulose. Most preferably, about 3 parts microcrystalline cellulose are used with about 30 parts sorbitol.

A flavorant is also present. Most preferably, the flavorant is a sweetener that is a mixture of saccharides such as maltodextrin and sucrose or fructose. These flavorants can comprise up to about 75 weight percent and more preferably comprise about 40 to about 60 weight percent of the final composition down to only a few percent when artificial sweeteners are used.

A preferred maltodextrin, which is a hydrolyzed cornstarch polymer having α-1→4-linked D-glucose having a dextrose equivalent (DE) of less than or equal to about 20, is the agglomerated product sold under the trademark MALTRIN QD. The MALTRIN QD products are sold by Grain Processing Corp., Muscatine, IA. Products are sold under the designations QD M440, M500 and M600 that have DE values of 4–7, 9–12 and 20–23, respectively.

The preferred MALTRIN QD™ M500 has a particle size specification that requires a minimal 90 percent passage through a U.S. #20 mesh sieve screen and a maximal 10 percent passsage through a U.S. #200 sieve screen. A typical particle size distribution provides 95 percent through a #20 sieve screen, 50 percent through a #60 sieve screen, 25 percent through a #100 sieve screen and 6 percent through a #200 sieve screen, U.S. Sieve Series.

These agglomerated maltodextrins have low bulk densities, e.g., MALTRIN QD M500 that is preferred has a bulk density of 34 g/100cc, are relatively non-friable and do not disintegrate readily in dry mixing. These materials also disperse very rapidly in water, e.g., 100 percent of a 15 weight percent mixture of MALTRIN QD M500 in water dissolves in one minute on mixing.

The agglomerated maltodextrin has a bland flavor that helps control sweetness and is also used as a bulking and flow control agent in the powder. On dissolution or dispersion in water, the agglomerated maltodextrin also contributes to building viscosity.

Sucrose or fructose (sugar) in finely divided form is a principal flavorant, and provides sweetness as is well known. An exemplary fructose is available from Roquette Corp., Gurnee, Ill.

It is preferred to use both the agglomerated maltodextrin and either sucrose or fructose as the flavorant, or part of the flavorant. It is also preferred to use about twice the amount of sugar as agglomerated maltodextrin. The combined amount of maltodextrin and sugar is used at about twice the amount of sorbitol.

Broadly, where sorbitol is present at about 20 to about 40 parts, the agglomerated maltodextrin can be present at about 10 to about 40 parts, and the sugar at about 10 to about 50 parts. With a preferred amount of about 25 to about 35 parts sorbitol, about 15 to about 25 parts agglomerated maltodextrin and about 30 to about 40 parts sugar are used. With the most preferred 30 parts sorbitol, about 20 parts agglomerated maltodextrin are used with about 37.5 parts sugar.

Artificial sweeteners such as aspartame, saccharin and cyclamates can also be used as flavorants in addition to or as replacements for the above flavorants. Dried fruit flavors such as orange and lemon flavors and other well known dry flavorants can also be used in place of some or all of the above flavorants.

As noted previously, the micronized terfenadine and Poloxamer are dry-blendedly dispersed into, onto and with the sorbitol to form a homogeneous material. Using a usual tumbling mixer, blender at a slow speed, this dispersal takes about 5–15 minutes. The other ingredients are then admixed and the admixture is blended for about another 5–15 minutes or until homogeneity is achieved.

Once all of the blending is completed, a freeflowing powder composition is obtained. The composition itself has preferably a pleasant taste, although whether the taste is pleasant or not is governed by the choice of the worker preparing the composition. The composition, more importantly, is substantially free from the taste of solubilized terfenadine when placed on the human tongue in the composition's dry form, or when tasted within about five minutes of being dispersed in water.

By being "substantially free from the taste of terfenadine" it is meant that an average person on tasting the composition would not detect the usually offensive dissolved terfenadine taste. This definition is meant not to be all-inclusive as some people may be particularly sensitive to the terfenadine taste so that no amount of masking will overcome that offensive taste. In addition, some discriminating palates such as those of chefs and other food experts who are used to discriminating one taste from another may be able to discern the distinctive bitter solubilized terfenadine taste. Generally, most people cannot discern the solubilized terfenadine taste in the completed composition.

The resulting powdered composition can be used as is for its antihistaminic effects by simply applying an antihistaminic amount of the composition upon the tongue and permitting the composition to disperse in saliva or with an appropriate drink. An antihistaminic amount of the powdered composition can also be dispersed with shaking or stirring in a few milliliters of water, e.g. about 5 to about 15 ml, and administered by drinking the dispersed composition. The composition can also be dispersed in a food such as applesauce, mashed bananas, peanut butter or the like and then ingested as those foods are normally ingested.

A contemplated powdered terfenadine oral composition can be packaged for sale as a powder in a suitable container or package such as a jar or bottle from which the user measures out his or her own antihistaminic dose, as with an appropriately sized spoon or similar device. More preferably, the powdered terfenadine is prepackaged in unit dose form so that each packaged unit contains a single antihistaminic dose as discussed before such as 15, 30, 94 60 mg of terfenadine. In one preferred embodiment, the unit dose is packaged in a tear-open packet from which the unit antihistaminic dose of terfenadine can be poured directly onto the tongue or into water or food as discussed before.

BEST MODE FOR CARRYING OUT THE INVENTION

Example 1

Terfenadine Oral Powder

A composition designed to provide 60 mg of terfenadine in 2 g of dry composition was prepared as follows.

The Sorbitol Instant™, maltodextrin and fructose used in the composition were separately sieved using a #60 U.S. Standard Sieve Screen, and only material that passed through the screen was used.

Micronized terfenadine (30 g) and the block co-polymer wetting agent (Pluronic™ polyol F-68) were mixed slowly in a "V-blender" for about five minutes. Sorbitol Instant™ (300 g) was added to the mixture and blended therewith for another five minutes to form a blend of all three components.

Microcrystalline cellulose (30 g; AVICEL™ CL-611) PVP (50 g, KOLLIDON™ K-90) maltodextrin (200 g, MALTRIN™ QD M500) and 375 g of fine, granular fructose were added to the above blend, and blending was continued for another ten minutes to form a homogeneous, dry terfenadine composition that was a free flowing powder.

The blended dry composition was thereafter packaged into 2 g sachets as unit doses.

Example 2

Taste Assay

A series of ten compositions was prepared using the general procedures described in Example 1. The resulting dry, powdered terfenadine compositions were then assayed by placing 0.5–2 g of the composition individually into the mouths of two experienced taste assayers. The amount of each sample used was determined based on the amount of terfenadine present in the individual samples so that the total amount of terfenadine remained approximately constant. The composition components are shown below in amounts by weight percent of the total composition. Taste ranking scores from each of the two assayers follow each assay of composition components.

TABLE

Composition Components in Weight Percents

| | | | | | | | | | | |
|---|---|---|---|---|---|---|---|---|---|---|
| Terfenadine, Micronized | 1.5 | 1.5 | 1.5 | 3.0 | 3.0 | 3.0 | 6.0 | 6.0 | 12.0 | 12.0 |
| Microncrystalline Cellulosic[1] | 3.0 | 3.0 | 3.0 | 3.0 | 3.0 | 3.0 | 3.0 | 3.0 | 3.0 | 3.0 |
| PVP[2] | 5.0 | 5.0 | 5.0 | 5.0 | 5.0 | 5.0 | 5.0 | 5.0 | 5.0 | 5.0 |
| Block Co-polymer[3] | 1.0 | 1.0 | 1.0 | 1.5 | 1.5 | 1.5 | 4.0 | 4.0 | 10.0 | 10.0 |
| Sorbitol Instant, fine | 30.0 | 30.0 | 30.0 | 30.0 | 30.0 | 30.0 | 30.0 | 30.0 | 30.0 | 30.0 |

TABLE-continued

| Composition Components in Weight Percents | | | | | | | | | | |
|---|---|---|---|---|---|---|---|---|---|---|
| Sucrose, fine | 39.5 |  | 20.0 | 37.5 |  | 20.0 | 37.0 |  | 20.0 |  |
| Maltodextrin[4], fine | 20.0 | 20.0 | 39.5 | 20.0 | 20.0 | 37.5 | 15.0 | 15.0 | 20.0 | 20.0 |
| Fructose, fine |  | 39.5 |  |  | 37.5 |  |  | 37.0 |  | 20.0 |
| Assayer #1 | 3 | 2 | 4 | 2 | 3 | 4 | 4 | 3 | 4 | 3 |
| Assayer #2 | 3 | 2 | 3 | 2 | 3 | 4 | 4 | 4 | 5 | 4 |

[1]AVICEL ™ CL-611 was used.
[2]KOLLIDON ™ K-90 was used.
[3]Poloxmer 188 was used.
[4]MALTRIN ™ QD M500 was used.

Numerical taste ranking values were as follows: 1=Excellent; 2=Very good; 3=Good; 4=Satisfactory; 5=Acceptable with slight bitter aftertaste; 6=Acceptable with slight soapy taste and bitter aftertaste; and 8=Bitter/unpleasant.

As is seen from the above results, each of the dry, powdered terfenadine-containing compositions was acceptable from a taste standpoint. In contrast, a crushed commercially available terfenadine tablet containing an equal amount of terfenadine provides a taste ranking score of about 6 or 7 under these assay conditions.

Although the present invention has now been described in terms of certain preferred embodiments, and exemplified with respect thereto, one skilled in the art will readily appreciate that various modifications, changes, omissions and substitutions may be made without departing from the spirit thereof.

We claim:

1. A dry, powdered terfenadine composition that comprises
   (a) a mixture of:
      (i) about 1 to about 20 parts by weight micronized terfenadine and
      (ii) about 0.2 to about 10 parts by weight a polyethylene oxide-polypropylene oxide-polyethylene oxide block copolymer having an HLB number of 24 that is a wetting agent for said terfenadine;
   that are dry-blendedly dispersed into:
   (b) about 20 to about 40 parts by weight spray-dried sorbitol particles that are loosely packed, randomly oriented filamentary crystals having pores that entrap said terfenadine particles and wetting agent upon said dry-blended dispersal, said components being further dry blended with
   (c) about 2 to about 10 parts by weight dry polyvinylpyrrolidone;
   (d) about 1 to about 5 parts by weight dry microcrystalline cellulose mixture that contains about 7 to about 20 weight percent sodium carboxymethylcellulose; and
   (e) a dry flavorant in an amount sufficient to provide a desired taste to said powder;
   said composition being a free-flowing powder that is substantially free from the taste of solubilized terfenadine when placed on the human tongue in dry form or when dispersed in water and tasted within about five minutes of said dispersal.

2. The composition according to claim 1 wherein said micronized terfenadine is present at bout 2 to about 10 parts by weight, said spray-dried sorbitol is present at about 25 to about 35 parts by weight and said block copolymer is present at about 1 to about 5 parts by weight.

3. The composition according to claim 1 wherein said polyvinylpyrrolidone is present at a weight ratio relative to said spray-dried sorbitol of about 1:10 to about 1:4.

4. The composition according to claim 1 wherein said microcrystalline cellulose mixture is present at a weight ratio relative to said sorbitol of about 1:20 to about 1:8.

5. The composition according to claim 1 wherein said flavorant powder comprises up to about 60 weight percent of said composition.

6. The composition according to claim 5 wherein said flavorant includes a sweetener.

7. A dry, powdered terfenadine composition that comprises
   (a) a mixture of:
      (i) about 2 to about 10 parts by weight micronized terfenadine and
      (ii) about 1 to about 5 parts by weight a polyethylene oxide-polypropylene oxide-polyethylene oxide block copolymer having an HLB number of 24 that is a wetting agent for said terfenadine;
   that are dry-blendedly dispersed into:
   (b) about 25 to about 35 parts by weight spray-dried sorbitol particles that are loosely packed, randomly oriented filamentary crystals having pores that entrap said terfenadine particles and wetting agent upon said dry-blended dispersal, said components being further dry blended with
   (c) about 3 to about 7 parts by weight dry polyvinylpyrrolidone;
   (d) about 2 to about 4 parts by weight dry microcrystalline cellulose mixture that contains about 7 to about 20 weight percent sodium carboxymethylcellulose; and
   (e) about 40 to about 60 parts by weight of a dry flavorant in an amount sufficient to provide a desired taste to said powder, said flavorant including a sweetener;
   said composition being a free-flowing powder that is substantially free from the taste of solubilized terfenadine when placed on the human tongue in dry form or when dispersed in water and tasted within about five minutes of said dispersal.

8. The composition according to claim 7 in unit dosage form in a package containing an antihistaminic dose of terfenadine.

* * * * *